May 5, 1959 S. O. VUICH Plant Pat. 1,831

PEACH TREE

Filed Oct. 21, 1958

WITNESS

Addison E. Avery

INVENTOR

Stella O. Vuich

Webster & Webster

ATTYS.

United States Patent Office

Plant Pat. 1,831
Patented May 5, 1959

1,831

PEACH TREE

Stella O. Vuich, Cutler, Calif.

Application October 21, 1958, Serial No. 768,818

1 Claim. (Cl. 47—62)

This discovery relates to a new and distinct variety of peach tree which bears relatively large, freestone peaches having white flesh spread with red near the stone, and cream colored skin attractively blushed with red.

The fruit of the present variety of peach tree is of excellent marketable equality for dessert use, and the flesh is characterized by moderate juice having a very sweet flavor suggestive of mild watermelon.

In comparison with other varieties of peach trees, the present variety bears fruit which has general resemblance to the Babcock (unpatented) but is larger in size and ripens approximately one month later; such ripening period being about with the yellow fleshed Rio Oso Gem (United States Plant Patent No. 84).

The present variety of peach tree is a chance seedling which I discovered growing in the yard of my ranch home located near Cutler, county of Tulare, State of California; the area in which the discovery was made being thus subject to my control, continued observation, and cultivation.

During the period of time that such chance seedling was growing toward maturity I gave it careful attention, and at the time of maturity I recognized the distinctive nature of the fruit borne by such tree.

Thereafter, the variety was successfully asexually reproduced by grafting onto a number of Rio Oso Gem peach trees in the family orchard adjacent my ranch home located as aforesaid; such reproductions—at maturity and when in bearing—having been found to run true to the parent tree in all respects.

Figures 1, 2:
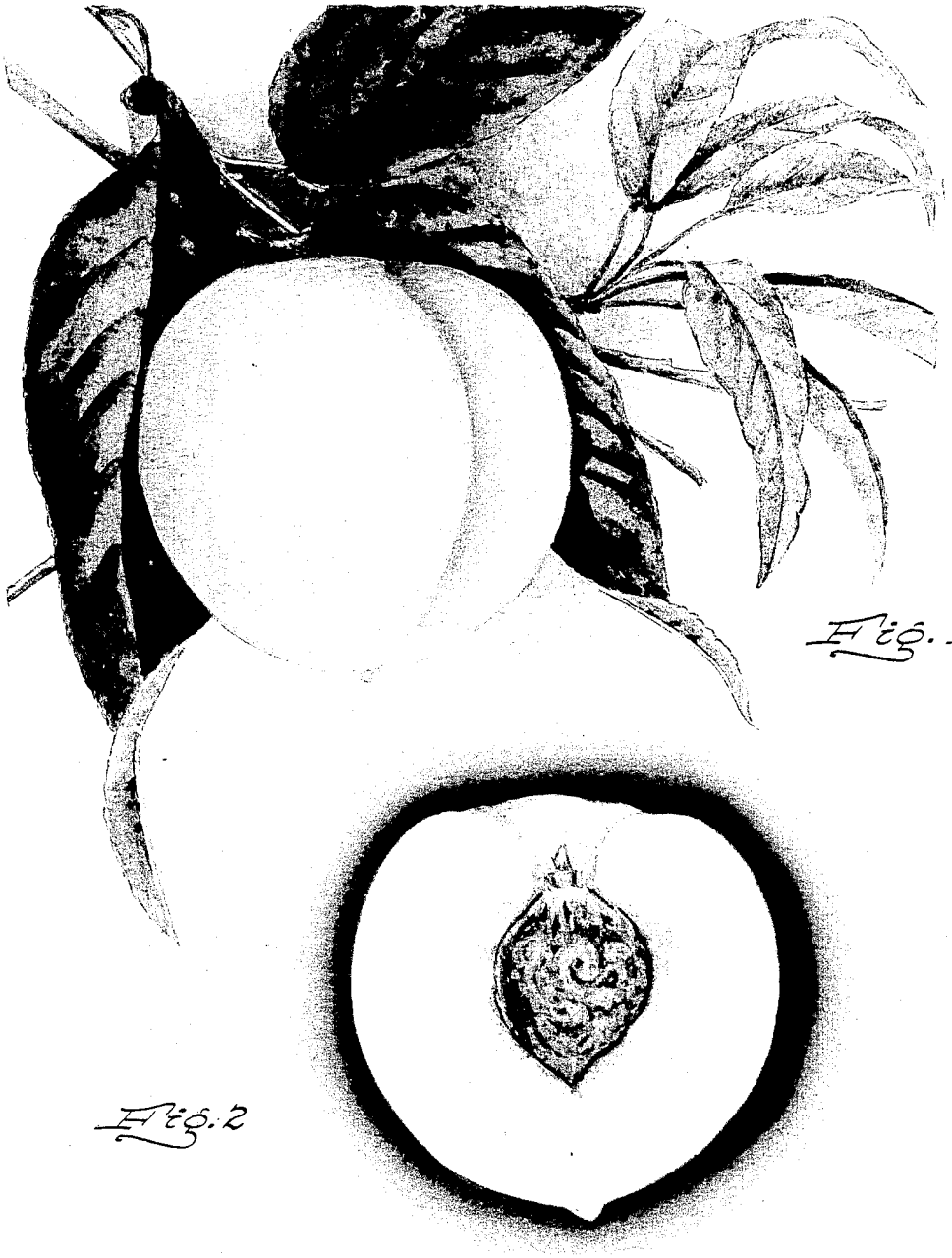
Fig. 1 is an elevation of one of the fruit, together with twigs and leaves.
Fig. 2 is a sectional elevation of one of the fruit, with the stone exposed.

Referring now specifically to the pomological details of this new and distinct variety of peach tree, the following is an outline description thereof; all major color plate identifications being by reference to Maerz and Paul dictionary of Color, except where common terms of color definition are employed:

Tree:
- *Size.*—Large.
- *Vigor.*—Vigorous.
- *Growth.*—Upright.
- *Density.*—Open.
- *Form.*—Vase shaped.
- *Hardiness.*—Hardy.
- *Production.*—Productive.
- *Bearing.*—Regular bearer.

Trunk:
- *Size.*—Medium.
- *Texture.*—Medium.

Branches:
- *Size.*—Medium.
- *Texture.*—Medium.
- *Color.*—Gray; Glossy.
- *Lenticels.*—Medium number; medium size.

Leaves:
- *Size.*—Medium. Average length, 8". Average width, 2".
- *Form.*—Obovate; lanceolate; acutely pointed.
- *Thickness.*—Medium.
- *Texture.*—Smooth.
- *Margin.*—Glandular; crenate.
- *Petiole.*—Medium length; medium thickness.
- *Glands.*—Average number—two to four. Small; reniform; green. Positioned most commonly on basal blade margin; otherwise on upper part of petiole.
- *Stipules.*—Linear; ephemeral.
- *Color (mature leaves).*—Top side—medium green (23–L–7). Under side—lighter green (22–J–6).

Flower buds:
- *Hardiness.*—Hardy.
- *Size.*—Medium.
- *Length.*—Medium.
- *Form.*—Plump.
- *Pubescence.*—Pubescent.

Flowers:
- *Blooming period.*—First and full bloom—February 18, 1958, and March 3, 1958, respectively. Early as compared with other varieties.
- *Size.*—Large.
- *Color.*—Pink.

Fruit:
- *Maturity when described.*—Eating ripe.
- *Date of first picking.*—July 24, 1958.
- *Date of last picking.*—August 6, 1958.
- *Size.*—Uniform. Medium to large—peaks in size between 48's and 54's. Average diameter axially, 3". Average transversely in suture plane, 3".
- *Form.*—Uniform; symmetrical; globose.
- *Suture.*—Distinct; shallow; slight depression beyond pistil point.
- *Ventral surface.*—Rounded; strongly lipped on both sides; lips equal.
- *Cavity.*—Rounded, with suture showing on one side.
- *Base.*—Rounded.
- *Apex.*—Short.
- *Pistil point.*—Apical.

Skin:
- *Thickness.*—Thin.
- *Toughness.*—Tender.
- *Tendency to crack.*—None.
- *Down.*—Scant; short; does not roll up when rubbed.
- *Color.* — Cream (9–C–2 — shading 9–E–3 to 10–H–3), blushed with red (4–J–9—shading in darker areas 6–K–10 to 6–L–10).

Flesh:
- *Amygdalin.*—Abundant.
- *Juice.*—Moderate.
- *Fibers.*—Few.
- *Ripens.*—Even.
- *Flavor.*—Delicate; suggestive of mild watermelon.
- *Aroma.*—Distinct.
- *Eating quality.*—Best.
- *Color.*—White (9–A–1—shading 9–C–1 to 9–D–1), mottled and streaked with red (3–K–7 to 3–L–7) next to stone.
- *Surface of pit cavity.*—Red with white and pink fibers.

Stone:
- *Type.*—Free.
- *Size.*—Small. Average length, 1⅜". Average breadth, 1⅛". Average thickness, ¾".
- *Form.*—Globose.
- *Base.*—Straight.
- *Sides.*—Equal.
- *Surface.*—Regularly furrowed throughout.

*Ridges.*—Rounded toward base; on either side.
*Pits.*—Elongated.
*Dorsal edge.*—Full, width deep narrow grooves toward base.
*Tendency to split.*—None.
*Color.*—Brown (7–E–12) shading to reddish purple (4–K–8) at base.

Use: Market; dessert.
Keeping quality: Good.
Shipping quality: Good.

The tree and its fruit herein described may vary in slight detail due to climatic and soil conditions under which the variety may be grown.

The following is claimed:

A new and distinct variety of peach tree, as illustrated and described, characterized by relatively large freestone fruit having flesh streaked and mottled with red next to the stone, by flesh having a very sweet flavor suggestive of mild watermelon, and by cream colored skin blushed with red; further characterized—in comparison with the white fleshed Babcock—by general resemblance but larger size and a ripening period approximately one month later; and further characterized—in comparison to the yellow fleshed Rio Oso Gem—by substantially the same ripening period.

No references cited.